United States Patent
Bacco et al.

(10) Patent No.: US 12,193,743 B2
(45) Date of Patent: Jan. 14, 2025

(54) OPHTHALMIC APPARATUS

(71) Applicant: Adaptica S.r.l., Padua (IT)

(72) Inventors: Paolo Bacco, Fiesso d'Artico (IT); Ivan Capraro, Belluno (IT); Gianluigi Meneghini, Selvazzano Dentro (IT)

(73) Assignee: ADAPTICA S.R.L., Padua (IT)

( * ) Notice: Subject to any disclaimer, the term of this patent is extended or adjusted under 35 U.S.C. 154(b) by 684 days.

(21) Appl. No.: 17/615,800

(22) PCT Filed: Feb. 26, 2020

(86) PCT No.: PCT/EP2020/054968
§ 371 (c)(1),
(2) Date: Dec. 1, 2021

(87) PCT Pub. No.: WO2020/178088
PCT Pub. Date: Sep. 10, 2020

(65) Prior Publication Data
US 2022/0287560 A1  Sep. 15, 2022

(30) Foreign Application Priority Data
Mar. 4, 2019 (IT) .......... 102019000003127

(51) Int. Cl.
*A61B 3/11* (2006.01)
*A61B 3/00* (2006.01)
*A61B 3/14* (2006.01)

(52) U.S. Cl.
CPC ............ *A61B 3/112* (2013.01); *A61B 3/0033* (2013.01); *A61B 3/14* (2013.01)

(58) Field of Classification Search
CPC ......... A61B 3/112; A61B 3/0033; A61B 3/14; A61B 3/10; A61B 3/0016; A61B 3/0091; A61B 3/11; A61B 3/111; A61B 3/113; A61B 3/117; A61B 3/1005; A61B 3/107; A61B 5/14555; A61B 5/163; A61B 8/10
(Continued)

(56) References Cited

U.S. PATENT DOCUMENTS 7,377,643 B1 * 5/2008 Chock .................... A61B 3/152
351/208
2007/0171363 A1 7/2007 Chen et al.
(Continued)

FOREIGN PATENT DOCUMENTS

CN 101548875 A 10/2009
CN 105530854 A 4/2016

OTHER PUBLICATIONS

International Search Report and Written Opinion issued Jun. 9, 2020 in Int'l Application No. PCT/EP2020/054968.
(Continued)

*Primary Examiner* — Travis S Fissel
(74) *Attorney, Agent, or Firm* — Rivka Friedman

(57) ABSTRACT

An ophthalmic apparatus for examining the eyes of a patient includes a housing arranged in such a way to define at least a chamber. The housing includes at least an observation opening adapted to allow a patient to observe an internal volume of said at least a chamber along at least a corresponding predefined optical path. The ophthalmic apparatus includes regulation means capable of continuously regulating the pupil diameter of at least an eye of the patient.

13 Claims, 7 Drawing Sheets

(58) Field of Classification Search
USPC .......................................................... 351/206
See application file for complete search history.

(56) References Cited

U.S. PATENT DOCUMENTS

| | | |
|---|---|---|
| 2008/0161716 A1 | 7/2008 | Livne et al. |
| 2012/0057130 A1 | 3/2012 | Naito |
| 2017/0000338 A1* | 1/2017 | Davis .................. A61B 3/0008 |
| 2018/0018516 A1* | 1/2018 | Odinokikh .......... G06V 40/193 |
| 2018/0064576 A1 | 3/2018 | Chen et al. |
| 2018/0279937 A1 | 10/2018 | Medberry et al. |
| 2018/0279948 A1* | 10/2018 | Medberry ............ A61B 5/4064 |

OTHER PUBLICATIONS

Int'l Preliminary Report on Patentability issued Aug. 25, 2021 in Int'l Application No. PCT/EP2020/054968.
Examination Report issued Oct. 14, 2022 in AU Patent Application No. 2020230889.

* cited by examiner

OPHTHALMIC APPARATUS

CROSS-REFERENCE TO RELATED APPLICATIONS

This application is a Section 371 of International Application No. PCT/EP2020/054968, filed Feb. 26, 2020, which was published in the English language on Sep. 10, 2020 under International Publication No. WO 2020/178088 A1, which claims priority under 35 U.S.C. § 119 to Italian Patent Application No. 102019000003127, filed on Mar. 4, 2019 the disclosures of all of which are incorporated herein by reference in their entireties.

The present invention refers to an improved ophthalmic apparatus.

The use of ophthalmic apparatuses to examine the eyes of a patient, for example to carry out optometrical measurements of the visual field or allow diagnosis of diseases, is widely known.

Some ophthalmic apparatuses are arranged to carry out measurements of values relating to the eyes of the patient, for example to measure refractive power, aberrations of the visual field, corneal curvature, intraocular pressure, and so forth.

Other ophthalmic apparatuses, such as "fundus cameras" or OCT/SLO ophthalmoscopes, are arranged to acquire images of the retina, for example colour or infrared images.

Generally, in the use of an ophthalmic apparatus to examine the eyes of a patient, the pupils of the patient must be in mydriatic condition, i.e., dilated with respect to a condition of normality.

Devices to obtain a dilation of the pupil diameter are known. An example is described in patent application US2008/0161716A1.

Devices of this type, currently available, often offer somewhat unsatisfactory performances that are generally not capable of providing a continuous regulation of the pupil diameter.

Moreover, these are typically "stand alone" devices, which cannot be integrated into a more complex ophthalmic apparatus.

At the state of the art, there is a great need for innovative solutions that are capable of providing advanced functions of regulation of the pupil diameter, preferably in association with other typical functions of ophthalmic apparatuses.

BRIEF SUMMARY OF THE INVENTION

The main aim of the present invention is to provide an ophthalmic apparatus that allows this need to be satisfied and, at the same time, reduces or overcomes the problems of the prior art set forth above.

Within this aim, an object of the present invention is to provide an ophthalmic apparatus capable of offering very high performances with regard to regulating the pupil diameter of the eyes of a patient. A further object of the invention is to provide an ophthalmic apparatus capable of associating the function of regulating, the pupil diameter with other functions for examining the eyes of the patient. A further object of the invention is to provide an ophthalmic apparatus that can be easily produced on an industrial scale, at costs competitive with prior art ophthalmic apparatuses.

This aim and these objects, together with other objects that will be more apparent from the subsequent description and from the accompanying drawings, are achieved according to the invention by an ophthalmic apparatus according to claim 1 and to the related dependent claims, set forth below.

In a general definition thereof, the ophthalmic apparatus according to the invention comprises a housing defining at least a chamber.

The aforesaid housing further comprises an observation opening adapted to allow a patient to observe an internal volume of said at least a chamber along at least a corresponding optical path of said ophthalmic apparatus.

The ophthalmic apparatus according, to the invention comprises regulation means of the pupil diameter of at least an eye of the patient.

These regulation means of the pupil diameter comprise:
  measuring means adapted to measure the pupil diameter of at least an eye of the patient, when the patient observes the internal volume of said at least a chamber;
  visible illumination means adapted to emit a visible light radiation in the internal volume of said at least a chamber and comprising at least a visible light source accommodated in said at least a chamber;
  control means operatively associated with said measuring means and with said visible illumination means.

The aforesaid control means are adapted to receive measuring data of the pupil diameter of at least an eye of the patient from said measuring means and to control operation of said visible illumination means depending on said measuring data.

According to an aspect of the invention, the aforesaid measuring means comprise:
  infrared illumination means adapted to emit an infrared light radiation in the internal volume of said at least a chamber and comprising at least an infrared light source accommodated in said at least a chamber;
  acquisition means adapted to acquire images of the pupil of at least an eye of the patient and comprising at least an acquisition unit accommodated in said at least a chamber and arranged along at least an optical path;
  processing means adapted to receive said images of the pupil of at least an eye of the patient and to provide said measuring data.

According to some embodiments of the invention, the aforesaid housing defines a single chamber.

According to these embodiments of the invention, the aforesaid measuring means comprise at least an infrared light source and an acquisition unit accommodated in the single chamber.

According to other embodiments of the invention, the aforesaid housing defines a pair of chambers distinct one from another.

According to these embodiments of the invention, the aforesaid measuring means comprise an infrared light source and an acquisition unit accommodated in each of said chambers.

According to some embodiments of the invention, the aforesaid housing comprises a single observation opening.

According to other embodiments of the invention, the aforesaid housing comprises a pair of observation openings distinct one from another.

According to an aspect of the invention, the aforesaid control means are adapted to carry out a first regulation procedure of the pupil diameter of at least an eye of the patient. Said first regulation procedure comprises the following steps:
  a.1) deactivating or maintaining deactivated said visible light source;
  a.2) acquiring said measuring data in such a way to acquire a first measured value of the pupil diameter;
  a.3) waiting for a predefined time interval;

a.4) acquiring again said measuring data in such a way to acquire a second measured value of the pupil diameter;

a.5) comparing said first measured value of the pupil diameter will said second measured value of the pupil diameter; if the pupil diameter increases:

a.6) comparing said second measured value of the pupil diameter with a first target value of the pupil diameter;

a.7) if said second measured value of the pupil diameter does not exceed said first target value of the pupil diameter, repeat said first regulation procedure;

a.8) if said second measured value of the pupil diameter exceeds said first target value of the pupil diameter, terminate said first regulation procedure; if the pupil diameter does not increase:

a.9) comparing said second measured value of the pupil diameter with said first target value of the pupil diameter;

a.10) if said second measured value of the pupil diameter does not exceed said first target value of the pupil diameter, terminate said first regulation procedure;

a.11) if said second measured value of the pupil diameter exceeds said first target value of the pupil diameter, terminate said first regulation procedure.

According to an aspect of the invention, the aforesaid control means are adapted to carry out a second regulation procedure of the pupil diameter of at least an eye of the patient. Said second regulation procedure comprises the following steps:

b.1) activating or maintaining activated said visible light source and commanding said visible light source to emit a visible light radiation with a reference value of light intensity;

b.2) acquiring said measuring data in such a way to acquire a third measured value of the pupil diameter;

b.3) waiting for a predefined time interval;

b.4) acquiring again said measuring data in such a way to acquire a fourth measured value of the pupil diameter b.5) comparing said third measured value of the pupil diameter with said fourth value of the pupil diameter; if the pupil diameter decreases:

b.6) comparing said fourth measured value of the pupil diameter with a second target value of the pupil diameter;

b.7) if said fourth measured value of the pupil diameter exceeds said second target value of the pupil diameter, repeating said second regulation procedure maintaining unchanged said reference value of light intensity;

b.8) if said fourth measured value of the pupil diameter is lower than or equal to said second target value of the pupil diameter, commanding said visible light source to emit a visible light radiation with a first new value of light intensity lower than said reference value of light intensity and repeating said second regulation procedure using said first new value of light intensity as new reference value of light intensity; if the pupil diameter does not decrease:

b.9) commanding said visible light source to emit visible light radiation with a second new value of light intensity higher than said reference value of light intensity and repeating said second regulation procedure using said second new value of light intensity as new reference value of light intensity.

According to an aspect of the invention, the ophthalmic apparatus comprises examination means of at least an eye of the patient operatively associated with said at least a chamber.

Said regulation means of the pupil diameter are capable of acting in cooperation with said examination means to carry out an examination procedure of at least an eye of the patient.

BRIEF DESCRIPTION OF THE DRAWINGS

Further features and advantages of the ophthalmic apparatus according to the invention will be more apparent with reference to the description given below and to the accompanying figures, provided purely for explanatory and non-limiting purposes, wherein.

DETAILED DESCRIPTION OF THE INVENTION

Figure 1:
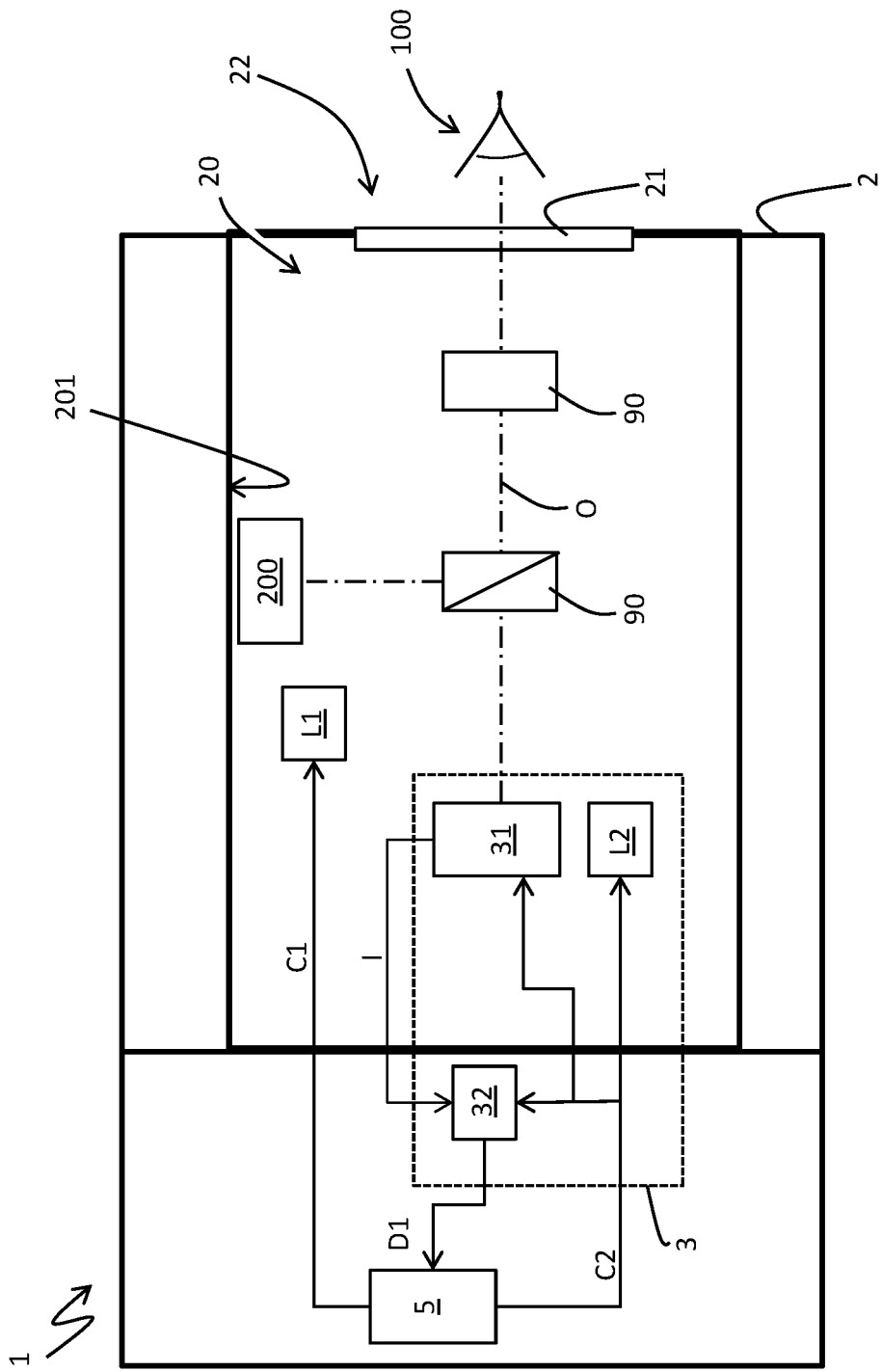
FIG. 1 schematically illustrates an embodiment of the ophthalmic apparatus according to the invention.

With reference to the aforesaid figures, the present invention relates to an ophthalmic apparatus 1 for examining at least an eye 100 of a patient.

The ophthalmic apparatus 1 according to the invention is characterized by comprising regulation means of the pupil diameter of at least an eye 100 of the patient.

A particularly important aspect of the ophthalmic apparatus 1 consists in the fact of comprising examination means 200 of the eye that can operate simultaneously to the aforesaid regulation means of the pupil diameter.

In this way, the ophthalmic apparatus 1 is advantageously capable of providing functions that require regulation of the pupil diameter to be successfully carried out, for example functions to measure the characteristic values of the eyes of the patient (refractive power, aberrations of the visual field, corneal curvature, intraocular pressure, etc.) or functions to acquire images of the retina (colour, infrared, fluorescence, etc.).

In general, the ophthalmic apparatus 1 can be both of monocular and binocular type and can comprise a single optical path or a pair of optical paths O, along which an eye or the eyes 100 of the patient are positioned, during use of said ophthalmic apparatus.

Each optical path O can be variously configured, according to needs. For example, each optical path O can have a rectilinear path or be configured as a broken line.

In use, the ophthalmic apparatus 1 can require a support, for example analogous to any other benchtop device, or be wearable by the user, for example in the manner of eyewear or a helmet.

The ophthalmic apparatus 1 comprises an external shaped housing 2 which defines an internal volume thereof.

In general, the housing 2, for example made of plastic material, can be variously configured, according to needs.

According to the invention, the housing 2 is arranged in such a way to define one or more chambers 20 internally.

The one or more chambers 20 are so-called "dark chambers" in the sense that during use of said ophthalmic apparatus, has in its internal volume luminance values lower than $10^{-4}$ nit ($cd/m^2$), in the absence of illumination by light sources.

Preferably, the one or more chambers 20 are intended shielded for close infrared and visible light, e.g. for light having wavelength values in the range between 400 nm and 1250 nm.

Figure 2:
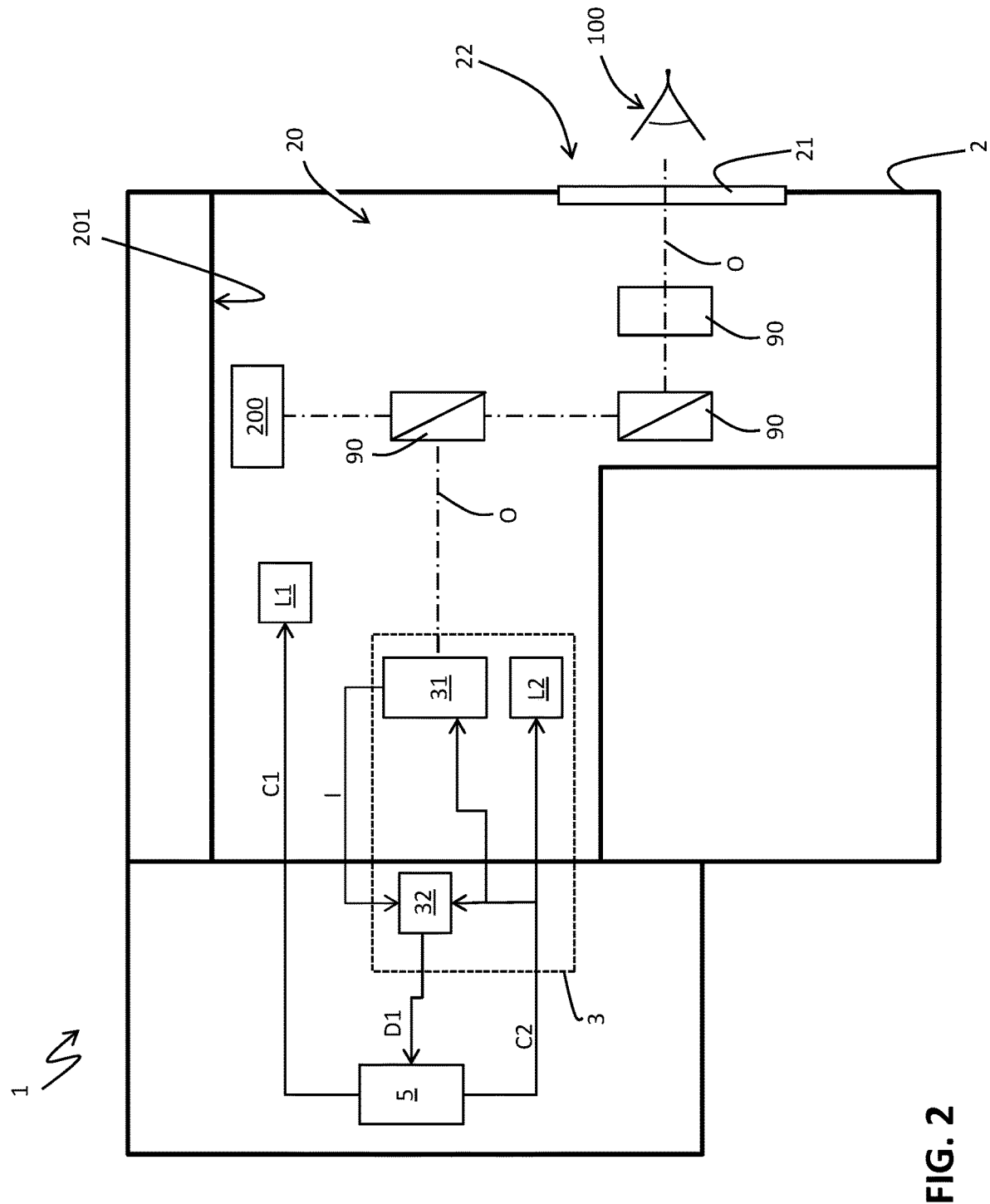
FIGS. 2-4 schematically illustrate some further embodiments of the ophthalmic apparatus according to the invention.
Figure 3:
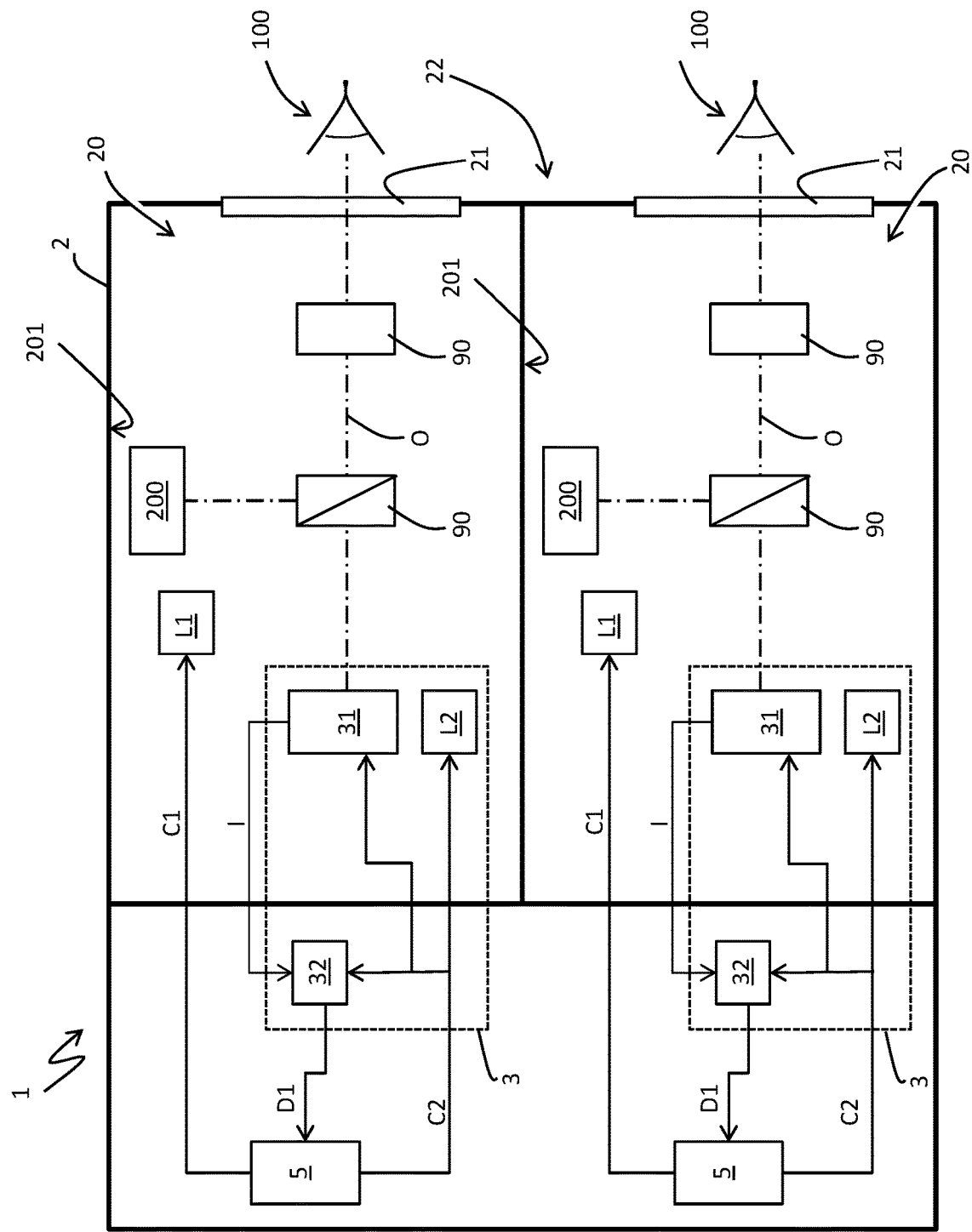
Figure 4:
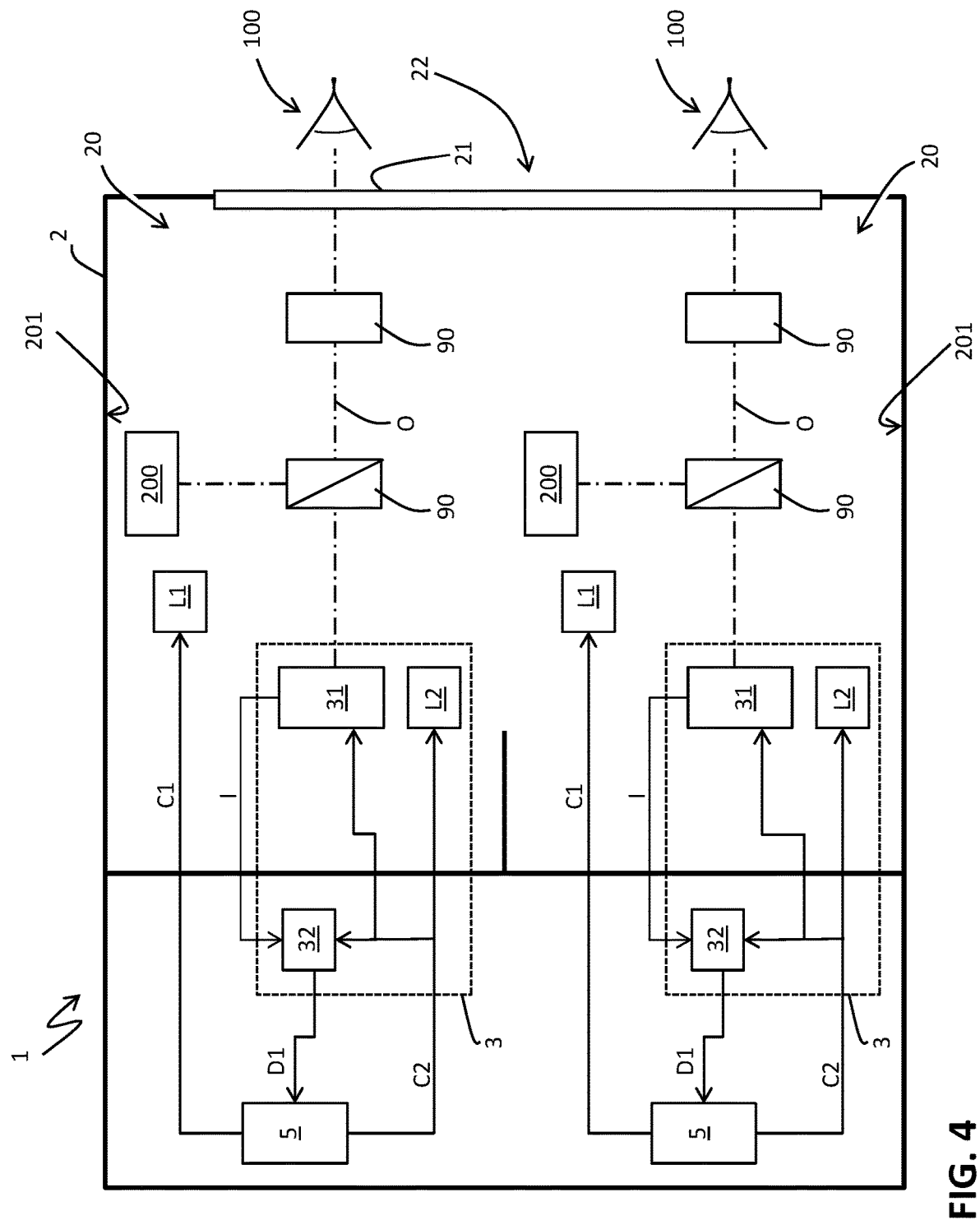

Each chamber 20 can be configured according to needs. For example, FIGS. 1, 3-4 show embodiments provided with chambers 20 with a substantially rectangular shaped section while FIG. 2 shows an embodiment provided with a chamber 20 with a substantially F-shaped section.

Preferably, each chamber 20 is defined by one or more walls 201 of the housing 2, which have anti-reflective surfaces, advantageously black in colour.

To produce the walls 201 with anti-reflective surfaces, know industrial processes and procedures can be used, for example plastic molding or co-molding procedures, painting or spray-painting, coating with layers of plastic or silicone materials, sand-blasting, shot-peening, or the like.

Preferably, if of monocular type, the ophthalmic apparatus 1 comprises a single chamber 20 (FIGS. 1-2) inside which an optical path O extends.

Preferably, if of binocular type, the ophthalmic apparatus 1 comprises a pair of chambers 20 distinct one from another (FIG. 3), inside each of which an optical path O extends.

However, in alternative embodiments of the invention, a single chamber 20 (FIG. 4) could be used, even when the ophthalmic apparatus 1 is of binocular type.

In this case, a pair of optical paths O extend inside the aforesaid chamber.

According to the invention, the housing 2 defines an observation interface 22 of the ophthalmic apparatus.

At this observation interface, the housing 2 comprises at least an observation opening 21 for access to said one or more chambers 20.

Each observation opening 21 is adapted to allow a patient to observe the internal volume of a chamber 20 along at least a corresponding optical path O maintaining the eye or the eyes in stable position during use of said ophthalmic apparatus.

Preferably, if the housing 2 is of monocular type, it comprises a single observation opening 21 (FIGS. 1-2) through which a patient can observe the internal volume of a chamber 20 along a corresponding optical path O.

Preferably, if the housing 2 is of binocular type, it comprises a pair of observation openings 21, at each of which a patient can observe the internal volume of a respective chamber 20 along a corresponding optical path O (FIG. 3).

In alternative embodiments of the invention, the housing 2 could however comprise a single observation opening 21, at which a patient can observe the internal volume of one or more chambers 20 along a pair of optical paths O (FIG. 4).

As can be easily understood by those skilled in the art, further variants of embodiment, all falling within the scope of the invention, are possible.

For example, the aforesaid one or more chambers 20 and observation openings 21 of the housing 2 and the aforesaid one or more optical paths O of the ophthalmic apparatus 1 could be variously configured differently to the description above.

Preferably, at the observation interface 22, the housing 2 comprises one or more shaped surfaces (not illustrated) on which the patient's face can rest during use of the ophthalmic apparatus.

Preferably, the ophthalmic apparatus 1 comprises a user interface (not illustrated) with which an operator can send commands or receive information.

This user interface can advantageously comprise a display for viewing data and suitable control keys, possibly of touch-screen type.

The user interface can if necessary be separated or separable with respect to the main body of the ophthalmic apparatus 1.

According to some embodiments of the invention, the ophthalmic apparatus 1 can comprise suitable communication ports for transmitting/receiving data to/from a remote computerized device. According to these embodiments of the invention, the ophthalmic apparatus 1 can be connectable with a portable computerized device which can if necessary be adapted to form the user interface of said apparatus.

Preferably, the ophthalmic apparatus 1 comprises a control unit adapted to control operation of said apparatus.

Advantageously, the control unit is operatively associated with the regulation means of the pupil diameter, with the examination means 200 of the eye and, if necessary, with the aforesaid user interface and communication ports.

Preferably, the control unit comprises one or more digital processing devices of the data, for example microprocessors or DSPs, capable of executing software instructions stored in suitable installed memories in order to implement the requested functions.

In any case, the control unit could advantageously also comprise suitable analog circuits operatively associated with said digital processing devices of the data.

Further variants for implementation of the control unit area are available to those skilled in the art.

As mentioned above, an essential aspect of the ophthalmic apparatus 1 consists in the fact that it comprises regulation means of the pupil diameter of the eyes of the patient.

According to the invention, the regulation means comprise measuring means 3 adapted to measure the pupil diameter of at least an eye 100 of the patient, when the patient observes the internal volume of a chamber 20.

Preferably, the measuring means 3 comprise:
infrared illumination means L2 adapted to emit an infrared light radiation in the internal volume of at least a chamber 20; and
acquisition means 31 adapted to acquire images of at least an eye of the patient and arranged along at least an optical path O of the ophthalmic apparatus 1; and
processing means 32 adapted to receive and process the aforesaid images I provided by the acquisition means 31 and to provide measuring data D1 of the pupil diameter of at least an eye of the patient.

Preferably, the infrared illumination means comprise at least an infrared light source L2 accommodated in the aforesaid at least a chamber 20.

Preferably, when the ophthalmic apparatus 1 is of monocular type and comprises a single chamber 20, the infrared illumination means comprise a single infrared light source L2 accommodated in the aforesaid chamber.

Preferably, when the ophthalmic apparatus 1 is of binocular type and comprises chambers 20 distinct one from another, the infrared illumination means comprise an infrared light source L2 accommodated in each chamber.

Preferably, when the ophthalmic apparatus 1 is of binocular type and comprises a single chamber 20, the infrared illumination means comprise one or more infrared light sources L2 accommodated in the aforesaid chamber along each optical path O of said ophthalmic apparatus.

Preferably, each infrared source L2 comprises an LED device adapted to emit infrared light and a corresponding electronic drive circuit adapted to drive the LED device in response to suitable control signals received.

Preferably, the aforesaid acquisition means comprise at least an acquisition unit 31 accommodated in the aforesaid at least a chamber 20.

Preferably, when the ophthalmic apparatus 1 is of monocular type and comprises a single chamber 20, the aforesaid acquisition means comprise a single acquisition unit 31 accommodated in the aforesaid chamber along an optical path O.

Preferably, when the ophthalmic apparatus 1 is of binocular type and comprises chambers 20 distinct one front another, the aforesaid acquisition means comprise an acquisition unit 31 accommodated in each chamber along a corresponding optical path O.

Preferably, when the ophthalmic apparatus 1 is of binocular type and comprises a single chamber 20, the aforesaid acquisition means comprise several acquisition units 31 accommodated in the aforesaid chamber, each along a corresponding optical path O of said ophthalmic apparatus.

Preferably, each acquisition unit 31 comprises a panel of CCD or C-MOS sensors, if necessary coupled to an optical assembly for receiving the light radiation, and a corresponding electronic interface circuit adapted to code and transmit the images I acquired by the panel of sensors. Preferably, the processing means 32 are included in the control unit of the ophthalmic apparatus. In this case, they can advantageously be formed of a processing component, preferably of digital type, of the aforesaid control unit.

Alternatively, the processing means 32 could be formed of an autonomous processing unit, preferably of digital type.

In the operation of the ophthalmic apparatus 1, to supply the measuring data D1, the measuring means 3 operate as follows.

The infrared illumination means L2 emit an infrared light in such a way to illuminate at least an eye 100 of the patient. The acquisition means 31 acquire images I of at least an eye of the patient and provide these images (suitably coded) to the processing means 32, The processing means 32 process the images I received from the acquisition means 32 and provide the measuring data. D1.

To process the images I relating to at least an eye of the patient, the processing means 32 can use suitable image processing algorithms of known type.

In general, the measuring means 3, in particular the infrared illumination means L2, the acquisition means 31 and the processing means 32, can be of known type and will be described in more detail below only in relation to the aspects that are important for the invention, for obvious reasons of brevity.

According to the invention, the regulation means of the pupil diameter comprise visible illumination means LI adapted to emit a visible light radiation in the internal volume of at least a chamber 20 in such a way to increase the luminance (with regard to visible light) of said at least a chamber.

The aforesaid visible illumination means comprise at least a visible light source LI accommodated in at least a chamber 20.

Preferably, when the ophthalmic apparatus 1 is of monocular type and comprises a single chamber 20, the visible illumination means comprise a single visible light source LI accommodated in the aforesaid chamber.

Preferably, when the ophthalmic apparatus 1 is of binocular type and comprises chambers 20 distinct one from another, the visible illumination means comprise a visible light source LI accommodated in each chamber.

Preferably, when the ophthalmic apparatus 1 is of binocular type and comprises a single chamber 20, the visible illumination means comprise one or more visible light sources LI accommodated in the aforesaid chamber.

Preferably, each visible light source comprises an LED device adapted to emit visible light and a corresponding electronic drive circuit adapted to drive the LED device in response to suitable control signals received.

In general, the aforesaid visible illumination means LI can be of known type and will be described in more detail below only in relation to the aspects that are important for the invention, for obvious reasons of brevity.

According to the invention, the regulation means of the pupil diameter comprise control means 5 operatively associated with the measuring means 3 and with the visible illumination means L1. The control means 5 are adapted to receive and process measuring data D1 of the pupil diameter of at least an eye 100 of the patient received from the measuring means 3 and are adapted to control operation of the visible illumination means L1 depending on the measuring data D1. Preferably, the control means 5 are adapted to provide first control signals C1 to control operation of the visible illumination means L1.

Preferably, the control means 5 are adapted to provide second control signals C2 to control operation of the measuring means 3, in particular of the infrared illumination means L2, of the acquisition means 31 and of the processing means 32.

Preferably, the control means 5 are included in the control unit of the ophthalmic apparatus. In this case, they can advantageously be formed of a processing component, preferably of digital type, of the control unit.

Alternatively, the control means 5 could be formed by an autonomous processing unit, preferably of digital type.

According to preferred embodiments of the invention, the control means 5 are configured to carry out suitable regulation procedures 50A, 50B of the pupil diameter of at least an eye 100 of the patient.

In general, during implementation of the aforesaid regulation procedures 50A and 50B, the control means 5 control operation of the visible illumination means (activation or deactivation of the light source LI) by sending suitable control signals C1 to the aforesaid illumination means.

To acquire the measuring data D1, the control means 5 provide suitable control signals C2 to control operation of the measuring means 3, in particular of the infrared illumination means L2, of the acquisition means 31 and of the processing means 32.

Preferably, the control means 5 are configured to initially carry out the first regulation procedure of the pupil diameter 50A and, subsequently, the second regulation procedure of the pupil diameter 50B. In principle, however, the regulation procedures 50A, 50B (in particular the regulation procedure 50A) could be carried out separately one from another (even if not simultaneously for obvious reasons that will be evident after illustrating their details).

For reasons of simplicity, the regulation procedures of the pupil diameter 50A, 50B are described here with reference to their implementation in an ophthalmic apparatus 1 of monocular type.

As can be easily understood by those skilled in the art, the regulation procedures of the pupil diameter 50A and 50B, described below, can be easily adapted for implementation in an ophthalmic apparatus 1 of binocular type.

First Regulation Procedure of the Pupil Diameter

In general, the first regulation procedure 50A of the pupil diameter is aimed at obtaining a dilation of the pupil of an eye 100 of the patient, i.e. to take the pupil of the eye 100 to a mydriatic condition. The control means 5 are therefore configured to carry out the first regulation procedure 50A maintaining the visible light source L1 deactivated (i.e. switched off) and, therefore, the chamber 20 at the lowest possible luminance value (in relation to visible light).

Figure 5:
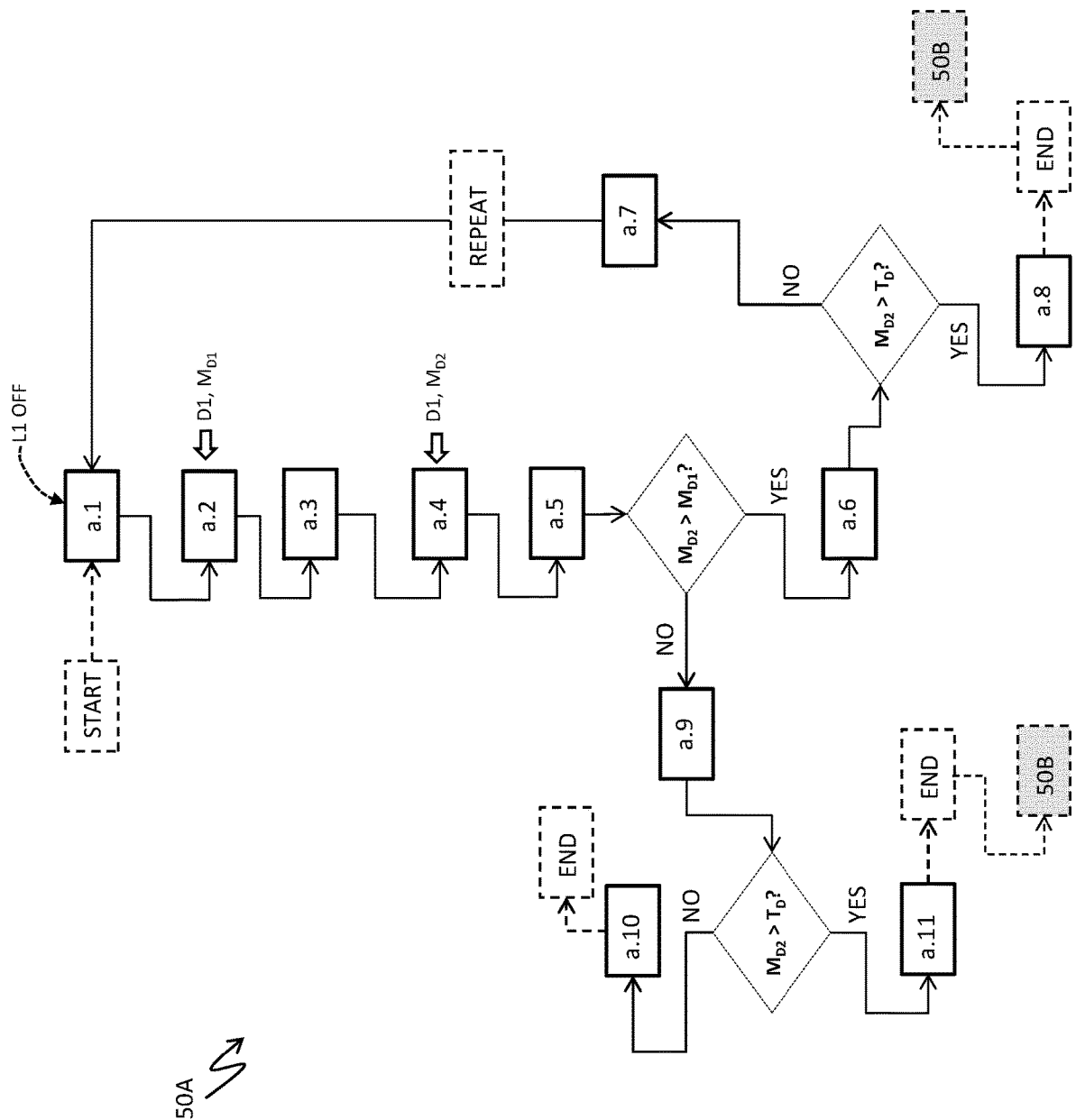
FIGS. 5-7 schematically illustrate the operation of the ophthalmic apparatus according to the invention.

With reference to FIG. 5, the regulation procedure 50A includes an initial step a.1) of deactivating or maintaining deactivated the visible light source L1.

The regulation procedure 50A includes a step a.2) of acquiring measuring data D1 of the pupil diameter of the eye of the patient. In this way, the control means 5 can acquire a first measured value Mm of the pupil diameter.

The regulation procedure 50A includes a step a.3) of waiting for a predefined time interval (for example a few seconds) in stand-by conditions. This step of the regulation procedure 50A is aimed at waiting for the pupil to dilate maintaining the eye of the patient in the dark (or rather in conditions of minimum ambient luminance).

The regulation procedure 50A includes a step a.4) of acquiring again the measuring data D1 in such a way to acquire a second measured value MD2 of the pupil diameter.

The regulation procedure 50A includes a step a.5) of comparing the first measured value Mm of the pupil diameter, acquired in step a.2), with the second measured value MD2 of the pupil diameter, acquired in step a.4).

An increase of the pupil diameter means that the eye 100 of the patient responds to the condition of dark in which it has been maintained during the aforesaid predefined time interval with a dilation of the pupil.

Therefore, if the value of the pupil diameter increases (i.e., MD2>Mm), the regulation procedure 50A comprises a step a.6) of comparing the second measured value of the pupil diameter MD2, acquired in step a.4), with a first target value Tm of the pupil diameter.

The first target value Tm of the pupil diameter can be a predefined value, for example memorized by the control unit. It can be a constant value or a value selectable through the user interface of the ophthalmic apparatus 1.

If the second measured value of the pupil diameter MD2 does not exceed the first target value Tm of the pupil diameter (i.e., $M_{D2}<=T_{D1}$ the regulation procedure 50A is repeated (step a.7).

The first target value Tm of the pupil diameter has not been reached and therefore sufficient dilation of the pupil of the eye 100 has not yet been obtained. Repetition of the regulation procedure 50A is aimed at obtaining further dilation of the pupil, if possible.

If the second measured value of the pupil diameter $M_{D2}$ exceeds the first target value $T_{D1}$ of the pupil diameter (i.e., $M_{D2}>T_{D1}$), the regulation procedure 50A is terminated (step a.8).

The first target value $T_{D1}$ of the pupil diameter has been reached and therefore sufficient dilation of the pupil of the eye 100 has been obtained. The regulation procedure 50A can be terminated. At this point, the second regulation procedure 50B of the pupil diameter (with the visible light source L1 activated), or a possible examination procedure of the eye 100 of the patient 100 by the examination means 200 of the eye, can be carried out.

If the step a.5) shows no increase of the value of the pupil diameter, this means that the eye does not respond to the substantial condition of dark in which it is maintained during the aforesaid predefined time interval with a dilation of the pupil.

If the value of the pupil diameter does not increase (i.e., $M_{D2}<=M_{D1}$), the regulation procedure 50A comprises a step a.9) of comparing the second measured value of the pupil diameter $M_{D2}$, acquired in step a.4), with the first target value $T_{D1}$ of the pupil diameter.

If the second measured value of the pupil diameter $M_{D2}$ does not exceed the first target value $T_{D1}$ of the pupil diameter (i.e., $M_{D2}<=T_{D1}$), the regulation procedure 50A is terminated (step a.10). This situation substantially indicates an error condition in which the regulation procedure 50A is substantially ineffective in obtaining sufficient dilation of the pupil diameter.

If the second measured value of the pupil diameter $M_{D2}$ exceeds the first target value $T_{D1}$ of the pupil diameter (i.e., $M_{D2}>T_{D1}$ the regulation procedure 50A is terminated (step a.11).

Even if the pupil of the eye 100 is not capable of dilating further, the first target value Tm of the pupil diameter has been reached and therefore sufficient dilation of the pupil has been obtained. The regulation procedure 50A can be terminated. At this point, the second regulation procedure 50B of the pupil diameter (with the visible light source L1 activated), or a possible examination procedure of the eye 100 of the patient 100 by the examination means 200 of the eye, can be carried out.

Second Regulation Procedure of the Pupil Diameter

In general, the second regulation procedure 50B of the pupil diameter is aimed at regulating with continuity the pupil diameter, in particular when sufficient dilation of the pupil of an eye 100 of the patient has been obtained (for example carrying out the regulation procedure 50A described above). The control means 5 are configured to carry out the second regulation procedure 50B maintaining the visible light source L1 activated and commanding it to emit visible light with different values of light intensity. During implementation of the second regulation procedure 50B, the chamber 20 will therefore have luminance values higher than the minimum obtainable value (with regard to visible light).

Figure 6:
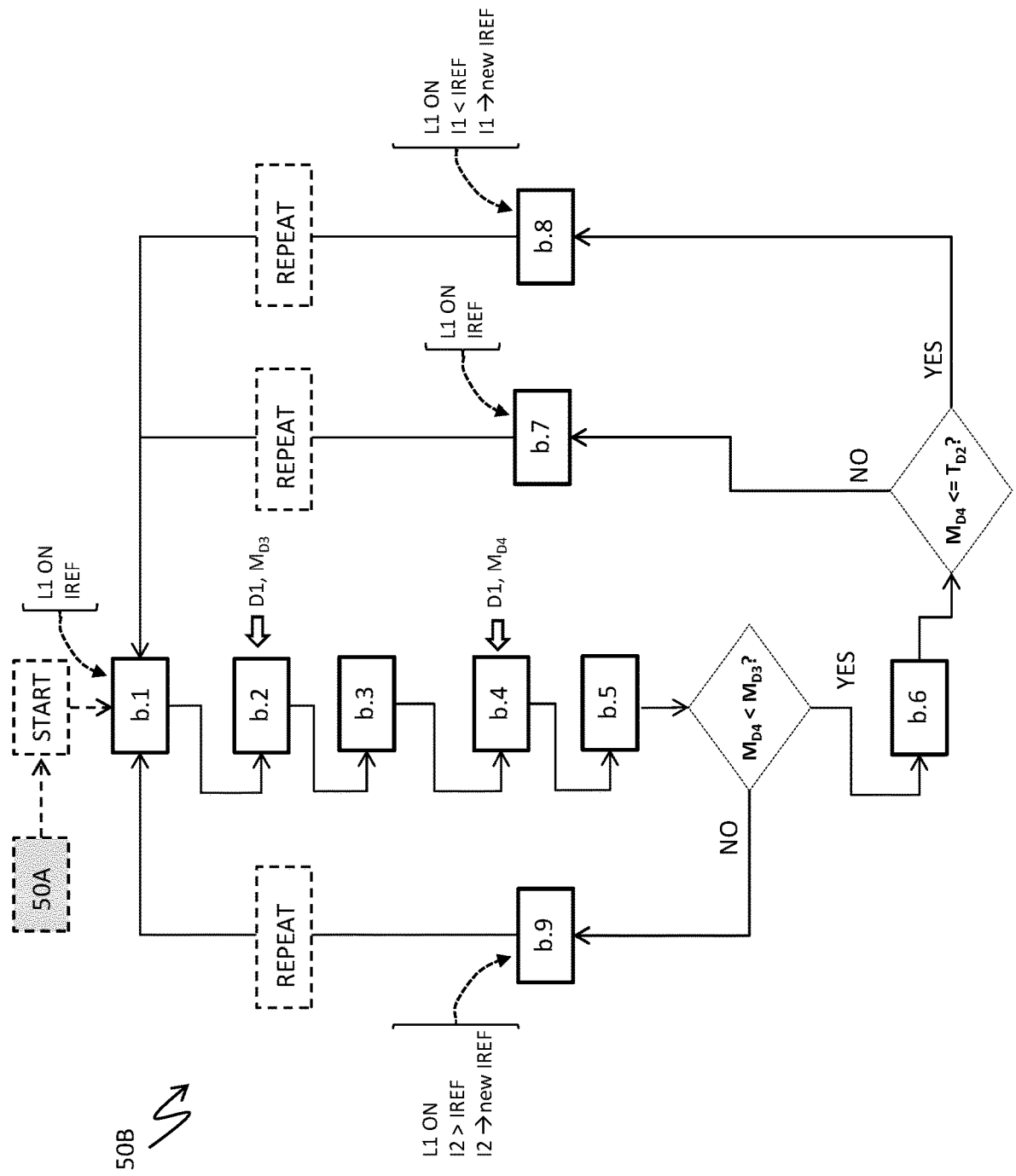

With reference to FIG. 6, the regulation procedure 50B includes an initial step b.1) of activating or maintaining activated the visible light source L1 and commanding the visible light source L1 to emit visible light with a reference value IREL of light intensity.

The regulation procedure 50B includes a step b.2) of acquiring measuring data D1 of the pupil diameter of the eye of the patient.

In this way, the control means 5 can acquire a third measured value MD3 of the pupil diameter. In general, this measured value differs from the other measured values acquired during the regulation procedures 50A and 50B.

The regulation procedure 50B includes a step b.3) of waiting for a second predefined time interval (for example a few seconds) in stand-by conditions.

This step of the regulation procedure 50B is aimed at waiting for the pupil to contract maintaining the eye 100 of the patient exposed to a visible light with a light intensity at the reference value IR. The regulation procedure 50B includes a step b.4) of acquiring again measuring data D1 of the pupil diameter of the eye of the patient.

In this way, the control means 5 can acquire a fourth measured value MD4 of the pupil diameter. In general, this measured value differs from the other measured values acquired during the regulation procedures 50A and 50B.

The regulation procedure 50B includes a step b.5) of comparing the third measured value MD3 of the pupil diameter, acquired in step b.2), with the fourth measured value Mm of the pupil diameter, acquired in step b.4).

A decrease of the pupil diameter means that the eye 100 of the patient responds to the condition of visible light in which it has been maintained during the aforesaid second predefined time interval with a contraction of the pupil.

Therefore, if the pupil diameter decreases (i.e., $M_{D4}<M_{D3}$), the regulation procedure 50B comprises a step b.6) of comparing the fourth measured value of the pupil diameter MD3, acquired in step b.4), with a second target value TD2 of the pupil diameter.

The second target value TD2 of the pupil diameter can be a predefined value, for example memorized by the control unit. It can be a constant value or a value selectable through a user interface of the ophthalmic apparatus 1.

Preferably, the second target value TD2 is lower than or equal to the first target value Tm used during the regulation procedure 50A.

If the fourth measured value of the pupil diameter Mm exceeds the second target value TD2 of the pupil diameter (i.e., $M_{D4}>T_{D2}$), the regulation procedure 50B is repeated (step b.7) maintaining the reference value IREF unchanged for the light intensity of the visible light emitted by the visible light source L1.

The second target value $T_{D2}$ of the pupil diameter has not been reached and therefore sufficient contraction of the pupil of the eye 100 has not yet been obtained. Repetition of the regulation procedure 50A is aimed at obtaining a further contraction of the pupil, if possible.

The light intensity IREF of the visible light emitted by the visible light source L1 can remain unchanged as the eye 100 of the patient has responded to the visible light having this value of light intensity during the aforesaid second predefined time interval with a contraction of the pupil.

If the fourth measured value of the pupil diameter MD4 is lower than or equal to the second target value TD2 of the pupil diameter (i.e., $M_{D4}<=T_{D2}$), the regulation procedure 50B comprises the step b.8) of commanding the visible light source L1 to emit visible light with a first new value I1 of light intensity lower than the reference value IREF of light intensity. The regulation procedure 50B is repeated using said first new value I1 of light intensity as new reference value IREF of light intensity. The second target value TD2 of the pupil diameter was reached and therefore sufficient contraction of the pupil of the eye of the patient was obtained. Repetition of the regulation procedure 50B, with a new lower reference value I1=IREF of light intensity for the visible light emitted by the visible light source L1, is aimed at preventing a further contraction of the pupil of the eye of the patient and at promoting a slight dilation.

If the preceding step b.5) shows a lack of decrease of the pupil diameter, this means that the eye did not respond to the visible light with a light intensity equivalent to the reference value IREF to which it was exposed during the aforesaid second predefined time interval with a contraction of the pupil. Therefore, if the pupil diameter does not decrease (i.e., $M_{D4}>=M_{D3}$), the regulation procedure 50B comprises a step b.9) of commanding the visible light source L1 to emit visible light with a second new value I2 of light intensity higher than the reference value IREF of light intensity. The regulation procedure 50B is therefore repeated using said second new value I2 of light intensity as new reference value IREF of light intensity.

If the pupil diameter does not decrease, it is not possible to reach the second target value $T_{D2}$ of the pupil diameter. Repetition of the regulation procedure 50B, with a new higher reference value I2=IREF of light intensity for the visible light emitted by the visible light source L1, is aimed at obtaining a further contraction of the pupil of the eye of the patient in such a way to make it possible to reach the second target value $T_{D2}$ of the pupil diameter.

As can be easily understood by those skilled in the art, further variants of embodiment of the regulation procedure 50A and 50B, all falling within the scope of the invention, are possible. Naturally, at each repetition of the regulation procedures 50A and 50B, the control means 5 acquire new measured values $M_{D1}$, $M_{D2}$, $M_{D3}$, $M_{D4}$ of the pupil diameter.

Advantageously, the target values $T_{D1}$, $T_{D2}$ of the pupil diameter could be modified according to needs, for example when the regulation procedures 50A and 50B are repeated.

Figure 7:
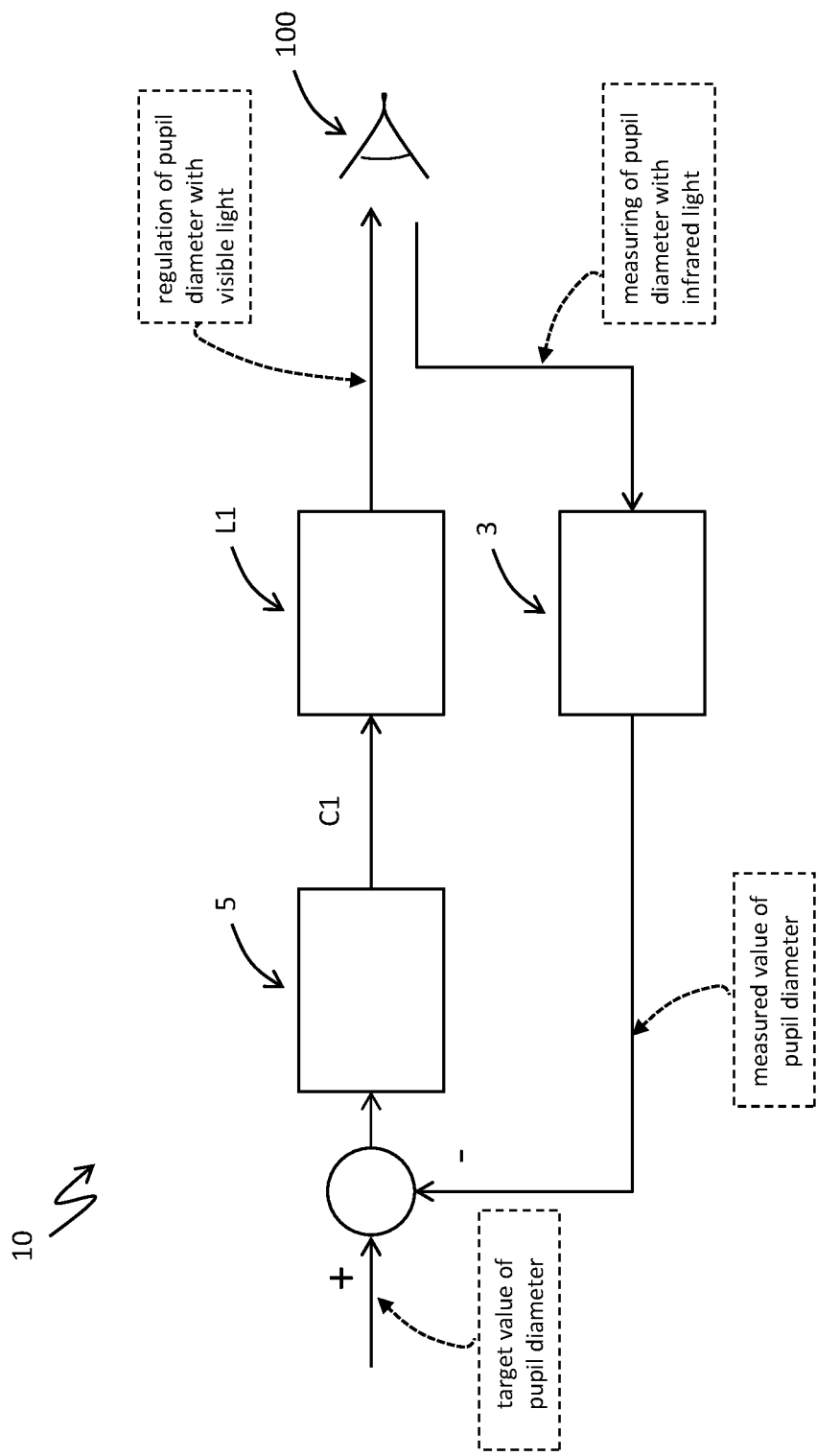

From the above, it is evident how the regulation means of the pupil diameter are capable of carrying out a continuous regulation, substantially in a closed loop, of the pupil diameter of at least an eye 100 of the patient (FIG. 7).

Implementation of the regulation procedures 50A, 50B, allows the above-mentioned regulation means to regulate the pupil diameter in such a way to track suitable target values $T_{D1}$, $T_{D2}$ selectable according to needs.

As mentioned above, according to preferred embodiments, the ophthalmic apparatus 1 comprises examination means 200 of the eye operatively associated with at least a chamber 20.

Preferably, if of monocular type and comprising a single chamber 20, the ophthalmic apparatus comprises the examination means 200 of the eye accommodated in the aforesaid chamber along the corresponding optical path O.

Preferably, if of binocular type and comprising chambers 20 distinct one from another, the ophthalmic apparatus 1 comprises the examination means 200 of the eye in each chamber along a corresponding optical path O. Preferably, if of binocular type and comprising a single chamber 20, the ophthalmic apparatus 1 comprises the examination means 200 of the eye accommodated in the aforesaid chamber, each along a corresponding optical path O of said ophthalmic apparatus.

The examination means 200 of the eye can comprise devices for measuring the characteristic values of the eyes of the patient (refractive power, aberrations of the visual field, corneal curvature, intraocular pressure, etc.), devices for acquiring images of the retina (colour, infrared, fluorescence, etc.), or parts of these devices included in the ophthalmic apparatus 1. In general, the aforesaid the examination means 200 of the eye can be of known type and will be described in more detail below only in relation to the aspects that are important for the invention, for obvious reasons of brevity.

In some embodiments of the invention (not illustrated), some components of the regulation means of the pupil diameter (for example the visible illumination means L1, the infrared illumination means L2 and the acquisition means 31) could be part of the examination means 200 of the eye included in the ophthalmic apparatus 1. This makes it possible to obtain greater structural and functional integration between the regulation means of the pupil diameter and the examination means 200 of the eye.

According to the aforesaid preferred embodiments of the invention, the regulation means of the pupil diameter are capable of cooperating with the examination means of the eye 100 to carry out an examination procedure of the eye.

They are therefore capable of performing the above-described functions of regulation of the pupil diameter during the implementation of a measuring or examination procedure of at least an eye 100 of the patient by the examination means 200 of the eye.

In practice, by carrying out the above-described regulation procedures 50A and 50B of the pupil diameter, the above-mentioned regulation means are capable of carrying out a continuous closed loop regulation of the pupil diameter in such a way to track target values $T_{D1}$, $T_{D2}$ of the pupil diameter that can advantageously be defined in such a way to allow the implementation of a measuring or examination procedure of at least an eye 100 of the patient by the examination means 200 of the eye. According to some embodiments of the invention, besides the regulation means of the pupil diameter and the aforesaid examination means of the eye 200, the ophthalmic apparatus 1 could comprise one or more optical elements 90 (for example beam splitters, lens assemblies, dichroic mirrors, lenses, etc.) accommodated in said at least a chamber 20, for example arranged along at least a corresponding optical path O.

As can be easily understood by those skilled in the art, further variants of embodiment of the ophthalmic apparatus 1, all falling within the scope of the invention, are possible.

For example, the regulation means of the pupil diameter could comprise alternative arrangements of the measuring means 3 (in particular of the infrared illumination means L2 and of the acquisition means 31), of the visible illumination means L1 and of the control means 5.

Operation of the ophthalmic apparatus 1 is illustrated in greater detail with reference to the embodiment of FIG. 1.

In use of the ophthalmic apparatus 1, the patient's face rests on the observation interface 22 in such a way to maintain an eye 100 in a predefined position at the observation opening 21.

The measuring means 3 cyclically carry out a measurement of the pupil diameter. At each measuring cycle, the infrared illumination means L2 illuminate the eye 100 with infrared light, the acquisition means 31 acquire one or more images I (infrared) of the eye 100 and transmit them to the processing means 32 which process the aforesaid images and provide the measuring data D1.

Depending on the measuring data D1, the control means 5 control operation of the visible illumination means to continuously (cyclically) regulate the pupil diameter of the eye 100 in such a way to track a target value of the pupil diameter. To this end, the control means 5 advantageously carry out the regulation procedures 50A, 50B.

Simultaneously to the above described regulation of the pupil diameter carried out by the regulation means of the pupil diameter, the examination means 200 of the eye carry out an examination procedure (for example measuring or acquiring images of the retina) of the eye 100.

The ophthalmic apparatus 1 according to the invention has considerable advantages with respect to prior art.

The ophthalmic apparatus 1 allows accurate continuous regulation of the pupil diameter to be carried out using a substantially closed loop regulation chain. Therefore, it is capable of offering very high performances in relation to controlling the pupil diameter of the eyes of a patient.

The ophthalmic apparatus 1 is capable of carrying out the aforesaid function of regulating the pupil diameter in a simple and direct manner, simultaneously to other functions of measuring or examining the eyes of the patient. Therefore, it is a multifunctional system that is relatively simple to use in practice.

The ophthalmic apparatus 1 can be easily produced on an industrial scale with components of known type, at competitive costs with the available prior art solutions.

The invention claimed is:

1. Ophthalmic apparatus (1) comprising:
  housing (2) defining at least a chamber (20), said housing comprising at least an observation opening (21) adapted to allow a patient to observe an internal volume of said at least a chamber along at least a corresponding optical path (O) of said ophthalmic apparatus;
  regulation means of the pupil diameter of at least an eye (100) of the patient comprising:
    measuring means (3) adapted to measure the pupil diameter of at least an eye (100) of the patient, when the patient observes the internal volume of said at least a chamber (20);
    visible illumination means adapted to emit a visible light radiation in the internal volume of said at least a chamber (20) and comprising at least a visible light source (L1) accommodated in said at least a chamber;
    control means (5) operatively associated with said measuring means (3) and said visible illumination means (L1), said control means being adapted to receive measuring data (D1) of the pupil diameter of at least an eye (100) of the patient from said measuring means (3) and to control operation of said visible illumination means (L1) depending on said measuring data (D1),
  wherein said control means (5) are adapted to carry out a first regulation procedure (50A) of the pupil diameter of at least an eye (100) of the patient, said first regulation procedure comprising:
    a.1) deactivating or maintaining deactivated said visible light source (L1);
    a.2) acquiring said measuring data (D1) in such a way to acquire a first measured value $M_{D1}$) of the pupil diameter;
    a.3) waiting for a predefined time interval;
    a.4) acquiring again said measuring data (D1) in such a way to acquire a second measured value ($M_{D2}$) of the pupil diameter;
    a.5) comparing said first measured value ($M_{D1}$) of the pupil diameter with said second measured value ($M_{D2}$) of the pupil diameter;
    if the pupil diameter increases:
    a.6) comparing said second measured value ($M_{D2}$) of the pupil diameter with a first target value ($T_{D1}$) of the pupil diameter;
    a.7) if said second measured value ($M_{D2}$) of the pupil diameter does not exceed said first target value ($T_{D1}$) of the pupil diameter, repeat said first regulation procedure; and
    a.8) if said second measured value ($M_{D2}$) of the pupil diameter exceeds said first target value ($T_{D1}$) of the pupil diameter, terminate said first regulation procedure.

2. Ophthalmic apparatus according to claim 1, wherein said measuring means (3) comprise:
  infrared illumination means adapted to emit an infrared light radiation in the internal volume of said at least a chamber (20) and comprising at least an infrared light source (L2) accommodated in said at least a chamber;
  acquisition means adapted to acquire images (I) of the pupil of at least an eye of the patient and comprising at least an acquisition unit (31) accommodated in said at least a chamber (20) and arranged along at least an optical path (O);
  processing means (32) adapted to receive said images (I) of the pupil of at least an eye (100) of the patient and to provide said measuring data (D1).

3. Ophthalmic apparatus, according to claim 1, wherein said housing (2) defines a single chamber (20).

4. Ophthalmic apparatus, according to claim 1, wherein said housing (2) defines a pair of chambers (20) distinct one from another.

5. Ophthalmic apparatus, according to claim 2, wherein said measuring means (3) comprise at least an infrared light source (L2) and an acquisition unit (31) accommodated in a single dark chamber (20).

6. Ophthalmic apparatus, according to claim 2, wherein said measuring means (3) comprise an infrared light source (L2) and an acquisition unit (31) accommodated in each of a pair of dark chambers (20).

7. Ophthalmic apparatus, according to claim 1, wherein said housing (2) comprises a single observation opening (21).

8. Ophthalmic apparatus, according to claim 1, wherein said housing (2) comprises a pair of observation openings (21) distinct one from another.

9. Ophthalmic apparatus, according to claim 1, wherein said first regulation procedure further comprises:
if the pupil diameter does not increase:
a.9) comparing said second measured value ($M_{D2}$) of the pupil diameter with said first target value ($T_{D1}$) of the pupil diameter;
a.10) if said second measured value ($M_{D2}$) of the pupil diameter does not exceed said first target value ($T_{D1}$) of the pupil diameter, terminate said first regulation procedure; a.11) if said second measured value ($M_{D2}$) of the pupil diameter exceeds said first target value ($T_{D1}$) of the pupil diameter, terminate said first regulation procedure.

10. Ophthalmic apparatus, according to claim 1, wherein said control means (5) are adapted to carry out a second regulation procedure (50B) of the pupil diameter of at least an eye (100) of the patient, said second regulation procedure comprising the following steps:
b.1) activating or maintaining activated said visible light source (L1) by commanding said visible light source (L1) to emit a visible light radiation with a reference value (IREF) of light intensity;
b.2) acquiring said measuring data (D1) in such a way to acquire a third measured value $M_{D3}$) of the pupil diameter;
b.3) waiting for a predefined time interval;
b.4) acquiring again said measuring data (D1) in such a way to acquire a fourth measured value ($M_{D4}$) of the pupil diameter;
b.5) comparing said third measured value ($M_{D3}$) of the pupil diameter with said fourth measured value ($M_{D4}$) of the pupil diameter;
if the pupil diameter decreases:
b.6) comparing said fourth measured value ($M_{D4}$) of the pupil diameter with a second target value ($T_{D2}$) of the pupil diameter;
b.7) if said fourth measured value ($M_{D4}$) of the pupil diameter exceeds said second target value ($T_{D2}$) of the pupil diameter, repeat said second regulation procedure maintaining unchanged said reference value (IREF) of light intensity;
b.8) if said fourth measured value ($M_{D4}$) of the pupil diameter is lower than or equal to said second target value ($T_{D2}$) of the pupil diameter, commanding said visible light source (L1) to emit a visible light radiation with a first new value (I1) of light intensity lower than said reference value (IREF) of light intensity and repeating said second regulation procedure using said first new value (I1) of light intensity as new reference value (IREF) of light intensity;
if the pupil diameter does not decrease:
b.9) commanding said visible light source (L1) to emit a visible light radiation with a second new value (I2) of light intensity higher than said reference value (IREF) of light intensity and repeating said second regulation procedure using second new value (I2) of light intensity as new reference value (IREF) of light intensity.

11. Ophthalmic apparatus, according to claim 1, further comprising an examination device (200) of at least an eye (100) of the patient operatively associated with said at least a chamber (20), said regulation means of the pupil diameter being capable of cooperating with said examination device (200) to carry out an examination procedure of at least an eye (100) of the patient.

12. Ophthalmic apparatus according to claim 5, wherein the dark chamber (20) has an internal volume luminance value lower than $10^{-4}$ nit (cd/m$^2$).

13. Ophthalmic apparatus according to claim 6, wherein the dark chamber (20) has an internal volume luminance value lower than $10^{-4}$ nit (cd/m$^2$).

* * * * *